United States Patent [19]

Greenwald

[11] Patent Number: 5,637,749

[45] Date of Patent: Jun. 10, 1997

[54] ARYL IMIDATE ACTIVATED POLYALKYLENE OXIDES

[75] Inventor: Richard B. Greenwald, Somerset, N.J.

[73] Assignee: Enzon, Inc., Piscataway, N.J.

[21] Appl. No.: 507,156

[22] Filed: Jul. 26, 1995

Related U.S. Application Data

[62] Division of Ser. No. 204,846, Mar. 2, 1994, abandoned, which is a division of Ser. No. 995,585, Dec. 22, 1992, Pat. No. 5,298,643.

[51] Int. Cl.$^6$ .................................................. C07C 249/02
[52] U.S. Cl. ................................. 558/6; 530/385; 604/20
[58] Field of Search .................... 558/6; 514/6; 530/385; 604/20

[56] References Cited

U.S. PATENT DOCUMENTS 5,478,806  12/1995  Nho ............................................ 514/6

*Primary Examiner*—Raymond Henley, III
*Assistant Examiner*—Keith MacMillan
*Attorney, Agent, or Firm*—Michael N. Mercanti

[57] ABSTRACT

Water-soluble aryl imidate activated polyalkylene oxides having improved hydrolytic stability and conjugates of the aryl imidate activated polyalkylene oxides with biologically active nucleophiles are disclosed. Methods of preparing the activated polyalkylene oxides and conjugates thereof are also disclosed.

20 Claims, No Drawings

ARYL IMIDATE ACTIVATED POLYALKYLENE OXIDES

This is a division of application Ser. No. 08/204,846, filed Mar. 2, 1994, now abandoned which, in turn is a division of application Ser. No. 07/995,585, filed Dec. 22, 1992, now U.S. Pat. No. 5,298,643.

BACKGROUND OF THE INVENTION

The present invention relates to aryl imidate activated polyalkylene oxides having improved hydrolytic stability, and to water-soluble polyalkylene oxide conjugates prepared therefrom.

The conjugation of water-soluble polyalkylene oxides with useful molecules such as proteins and polypeptides is well known. The coupling of peptides and polypeptides to polyethylene glycol (PEG) and similar water-soluble polyalkylene oxides is disclosed by U.S. Pat. No. 4,179,337 to Davis et al.

Davis et al. discloses that physiologically active polypeptides modified with PEG exhibit dramatically reduced immunogenicity and antigenicity. Also, the polyalkylene oxide conjugates, when injected into a living organism, have been shown to remain in the bloodstream considerably longer than the corresponding native proteins. Accordingly, a number of polyalkylene oxide conjugated therapeutic proteins have been developed exhibiting reduced immunogenicity and antogenicity and longer clearance times, while retaining a substantial portion of the protein's physiological activity. Significant polyalkylene oxide conjugated therapeutic proteins include tissue plasminogen activator, insulin, interleukin II and hemoglobin.

The utility of polyalkylene oxide conjugation is not limited to the modification of proteins and polypeptides. Activated polyalkylene oxides will react with essentially any nucleophile. The coupling of polyalkylene oxides with oligonucleotides is disclosed by U.S. Pat. No. 4,904,582 to Tullis. U.S. Pat. No. 5,160,734 discloses sustained release formulations of polyalkylene oxides coupled with dihydropyridine calcium channel blockers.

To conjugate polyalkylene oxides, the hydroxyl endgroups of the polymer must first be converted into, that is, substituted with, reactive functional groups. This process is frequently referred to as "activation" and the product is called an "activated polyalkylene oxide."

Until recently, covalent attachment of the polyalkylene oxide to an appropriate nucleophile was effected by activated polyalkylene oxides such as polyalkylene oxide succinoyl-N-hydroxy succinate, as disclosed by Abuchowski et al., *Cancer Biochem. Biophys.*, 7, 175–86 (1984). This polyalkylene oxide derivative is desirable because it is reactive under mild conditions.

A shortcoming associated with this derivative, however, is the fact that it is relatively hydrolytically unstable when no nucleophile is present. Recently, in U.S. Pat. No. 5,122,614, polyalkylene oxide-N-succinimide carbonates were disclosed having improved hydrolytic stability over the polyalkylene oxide succinoyl succinates. Even so, these active esters undergo hydrolysis under the pH conditions necessary to deprotonate the epsilon-$NH_2$ groups of polypeptide lysines for conjugation, which subject the activated polyalkylene oxide to hydroxyl attack. This does not affect the reaction end product, other than to reduce its yield. While reduced yields ordinarily affect product cost, the hydrolysis becomes even more costly for several reasons. Firstly, reaction mixtures cannot be prepared significantly in advance. Additional purification of the end product is required to remove the hydrolytic degradation products. Furthermore, the reduction in yield is compensated for by increasing the amount of activated polyalkylene oxide starting material. This increases the viscosity of the reaction mixture, thereby further increasing the processing cost, and potentially interferes with downstream purification of the polymer and conjugate.

There remains a need for hydrolytically stable activated polyalkylene oxides. One group of newly developed polyalkylene oxides is the polyalkylene oxide alkyl imidates of U.S. Pat. No. 4,791,192. However, Hunter et al., *J. Amer. Chem. Soc.*, 84, 3491–504 (1962) and Browne et al., *Biochem. and Biophys. Res. Comm.*, 67(1), 126–32 (1975) studied the use of simple alkyl imidates to modify the primary amines of proteins and other small molecules and reported the alkyl imidates to be hydrolytically unstable at protein reaction conditions. Hunter et al., however, reported simple aryl imidates to be hydrolytically stable. Aryl imidate activated polyalkylene oxides are unreported.

SUMMARY OF THE INVENTION

It has now been discovered that polyalkylene oxides activated by substitution with an aryl imidate moiety possess a desirable combination of nucleophilic reactivity and hydrolytic stability. For the conjugation of polyalkylene oxides with polypeptides, the desired aminolysis predominates over hydrolysis, so that reactions with proteins in aqueous solutions occur with higher yields. The aryl imidate activated polyalkylene oxides have improved resistance to hydroxyl attack under the pH conditions which are required in order to deprotonate the protein amines.

Therefore, in accordance with the present invention there is provided a water-soluble aryl imidate activated polyalkylene oxide. Preferred aryl imidate activated polyalkylene oxides are represented by the structure of Formula I:

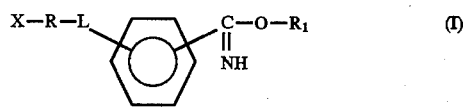

wherein

R is a water-soluble polyalkylene oxide;

L is a moiety forming a hydrolytically stable, covalently bonded linkage between the polyalkylene oxide and the phenyl ring of the aryl imidate;

$R_1$ is a moiety selected from alkyl, phenyl, phenylalkyl and cycloalkyl moieties; and X is a terminal moiety of the polyalkylene oxide.

In accordance with the present invention, there is also provided a process for the preparation of water-soluble aryl imidate activated polyalkylene oxides, which process includes the steps of:

reacting a benzonitrile-capped polyalkylene oxide with an alcohol in the presence of anhydrous hydrogen chloride gas, so that an aryl imidate activated polyalkylene oxide is formed; and recovering said aryl imidate activated polyalkylene oxide.

The aryl imidate activated polyalkylene oxides of the present invention react with biologically active nucleophiles to form conjugates thereof covalently bonded by linkages containing imino moieties. When the biologically active nucleophile is a protein or polypeptide, conjugation occurs at the epsilon-$NH_2$ moieties of lysines to form a linkage containing a stable amidate moiety.

The present invention therefore also provides a method of forming a biologically active conjugate of a biologically active nucleophile and one or more water-soluble polyalkylene oxides covalently bonded thereto, which method includes the steps of:

contacting the nucleophile with an aryl imidate activated polyalkylene oxide, so that a biologically active conjugate of the biologically active nucleophile and the polyalkylene oxide is formed; and recovering the biologically active conjugate.

The present invention thus also provides a biologically active conjugate of a nucleophile having biological activity and one or more water-soluble polyalkylene oxides covalently bonded thereto by a linkage formed by reacting the nucleophile with an aryl imidate activated polyalkylene oxide.

The biologically active conjugates of the present invention possess numerous therapeutic applications. The present invention therefore also provides a method of treatment in which a mammal in need thereof is administered a therapeutically effective amount of the biologically active conjugates of the present invention.

The hydrolytic stability of the aryl imidate activated polyalkylene oxides of the present invention permit bulk solutions of activated polyalkylene oxide to be prepared in advance of production runs. Furthermore, the aryl imidate group can be reacted with a variety of biologically active nucleophiles of interest other than lysine epsilon amino groups of polypeptides. For example, the aryl imidates will react with any polypeptide nucleophile, including cysteine mercapto groups. In addition, the aryl imidates are also reactive with nucleotides such as guanine, adenine, and the like, and derivatives thereof which possess nucleophilic amino groups.

DETAILED DESCRIPTION OF THE PREFERRED EMBODIMENT

The aryl imidate activated polyalkylene oxides of the present invention must be prepared from polyalkylene oxides that are soluble in water at room temperature. Polyalkylene oxides meeting this requirement are polyethylene glycol (PEG) and copolymers thereof. Block copolymers of PEG with polypropylene glycol or polypropylene oxide are also suitable for use with the present invention, provided that the degree of block copolymerization is not so great as to render the polymer insoluble in water at room temperature.

The molecular weight of the polymer will depend mainly upon the end use of a particular polymer conjugate. Those of ordinary skill in the art are capable of determining molecular weight ranges suitable for their end-use applications. In general, the useful range of molecular weight is a number average molecular weight between about 600 and about 100,000 daltons, and preferably between about 2,000 and about 20,000 daltons. A molecular weight of 5,000 daltons is most preferred.

Preferred aryl imidate activated polyalkylene oxides are represented by the structure of Formula I, wherein R is a water-soluble polyalkylene oxide, L is a moiety forming a hydrolytically stable, covalently bonded linkage between the polyalkylene oxide and the phenyl ring of the aryl imidate, $R_1$ is a moiety selected from alkyl, phenyl, phenylalkyl, cycloalkyl, and the like, and X is a terminal moiety of the polyalkylene oxide.

The aryl imidate activated polyalkylene oxides of the present invention, including those depicted by Formula I, are usually recovered in the form of an imidate salt, typically a hydrochloride or hydrobromide salt. Therefore, the polyalkylene oxide aryl imidates of the present invention are defined as including the imidate salts thereof.

X can be a group into which a terminal hydroxyl group may be converted, including the reactive derivatives of the prior art disclosed in U.S. Pat. Nos. 4,179,337, 4,847,325, 5,122,614 and in and commonly owned U.S. patent application Ser. No. 626,696, filed Mar. 18, 1991, the disclosures of all of which are hereby incorporated herein by reference thereto. The heterobifunctional polymers can be prepared by methods known to those skilled in the art without undue experimentation.

X can thus also be an aryl imidate derivative having the structure of Formula II:

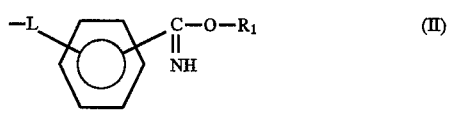

(II)

wherein L and $R_1$ are the same as disclosed above with respect to Formula I. When the moieties selected for L and $R_1$ on both ends of the polymer are identical, the polymer will then be a symmetrical, homobifunctional polymer derivative.

Such double polymer substitution can result in either intra- or intermolecular crosslinking of the nucleophile, which, in some cases, can be useful. Such crosslinking can be controlled by the amount of polymer used and the concentration of reacting species, which methods are well-known to those of ordinary skill in the art.

Crosslinking can also be prevented by using a pre-block polymer having only one labile hydroxyl group per polymer moiety. In such polymers, X would represent a blocking group such as an alkoxy group of one to four carbon atoms. The preferred blocking group is a methoxy group. For the preparation of homobifunctional and monofunctional polymer derivatives, see Buckmann et al., *Makromol. Chem.*, 182(5), 1379–84 (1981). X can also represent an antibody or solid support covalently coupled to the polymer by methods known to those skilled in the art as illustrated in EP 295,073.

The moieties represented by L that are capable of forming a hydrolytically stable covalently bonded linkage between a polyalkylene oxide and the phenyl ring of a aryl imidate are well-known to those of ordinary skill in the art. Examples of L include —$R_2$— and —$R_2$—$(CH_2—)_zR_3$—, wherein Z is an integer from one to six, inclusive, and $R_2$ and $R_3$ are moieties independently selected from amide, urea, urethane, ether, secondary amine and imidate moieties.

The aryl imidate activated polyalkylene oxides of the present invention are formed by reacting a benzonitrile-capped polyalkylene oxide with an alcohol in the presence of anhydrous hydrogen chloride gas. For example, to obtain the aryl imidate activated polyalkylene oxide of Formula I, an alcohol represented by the formula $R_1OH$, wherein $R_1$ is the same as described above with respect to Formula I is reacted with a benzonitrile capped polyalkylene oxide represented by the structure of Formula III:

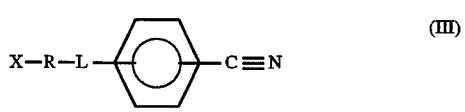

(III)

wherein R, L and X are the same as described above with respect to Formula I. The resulting aryl imidate has improved hydrolytic stability, but yet is capable of undergoing nucleophilic displacement of the —$OR_1$ moiety. $R_1$ is preferably a methyl, ethyl, phenyl, benzyl or cyclohexyl moiety.

The reaction is carried out in a solvent in which the reactants are soluble, such as methanol. A reaction temperature between 0° C. and 10° C. is suitable, and a temperature between 5° C. and 8° C. is preferred. All materials must be essentially free of water. Scrupulous care must be taken not to contaminate the reaction mixture with water.

The benzonitrile capped polyalkylene oxides of the present invention are formed by reacting a polyalkylene oxide or a functionalized polyalkylene oxide with a substituted benzonitrile. Other reactants may also be required. The selection of a polyalkylene oxide, functionalized polyalkylene oxide, substituted benzonitrile, and other reactants to obtain the desired L group is well understood by those of ordinary skill in the art.

For example, a urethane linkage can be obtained for L by reacting a polyalkylene oxide with a benzonitrile isocyanate. A urethane group can also be obtained by reacting a polyalkylene oxide isocyanate with a hydroxy benzonitrile. Polyalkylene oxide isocyanates are obtained by reacting polyalkylene oxide amines, which are commercially available, with phosgene. A diurethane linkage can be obtained for L by reacting an alkyl diisocyanate such as hexamethylene diisocyanate, with a polyalkylene oxide and a hydroxybenzonitrile.

A two-step reaction familiar to those skilled in the art is required to prevent double polyalkylene oxide or double hydroxybenzonitrile substitution of the diisocyanate. The polyalkylene oxide is added to an excess of diisocyanate, so that an isocyanate capped polyalkylene oxide is formed as the predominant reaction product from which the significantly lower molecular weight unreacted diisocyanate is readily removed. The isocyanate capped polyalkylene oxide is then reacted with the hydroxy benzonitrile.

An ether or secondary amine linkage can be obtained for L by reacting a polyalkylene oxide substituted with a moiety capable of undergoing nucleophilic displacement in the presence of a base with a hydroxy or amino benzonitrile. Polyalkylene oxide tosylates are preferred, which are prepared by reacting polyalkylene oxides with toluenesulfonyl chloride in a well-known reaction. See, e.g., the procedure of Mutter, *Tetrahedron Lett.*, 31, 2839–42 (1978). Other suitable polyalkylene oxides are polyalkylene oxide mesylates and polyalkylene oxide triflates which are prepared similarly. The ether linkage is formed by reacting the substituted polyalkylene oxide with hydroxybenzonitrile, and the secondary amine linkage is formed by reacting the activated polyalkylene oxide with aminobenzonitrile.

The formation of an amide linkage for L is also essentially conventional and can be obtained by reacting polyalkylene oxide amines, which are commercially available, with carboxybenzonitriles, or by reacting polyalkylene oxide carboxylic acids with aminobenzonitriles. Polyalkylene oxide carboxylic acid chlorides are commercially available (Aldrich Chemical) and can also be prepared by the method disclosed by Buckmann et al., *Makromol. Chem.*, 182(5), 1379–84 (1981). The acid chloride is readily converted to the carboxylic acid by well-known, conventional methods. Diamide linkages can be formed by reacting alkyl diamines with polyalkylene oxide carboxylic acids and carboxybenzonitriles using the above-described two-step reaction, or by reacting polyalkylene oxide amines and aminobenzonitriles with a dicarboxylic acid such as malonic acid, succinic acid, glutaric acid, maleic acid, fumaric acid or phthalic acid.

The diamide can also be formed by reacting the polyalkylene oxide amines and aminobenzonitriles with an acid anhydride such as succinic anhydride, maleic anhydride or phthalic anhydride, again using a two-step reaction. The carboxylic acids, dicarboxylic acids or acid anhydrides should either first be converted to acid chlorides, or else reacted with the amines or diamines in a carbodiimide mediated coupling reaction.

The formation of a urea linkage for L is obtained by reacting a polyalkylene oxide amine with a benzonitrile isocyanate, or by reacting a polyalkylene oxide isocyanate with an aminobenzonitrile. Diurea linkages can be formed by reacting alkyl diisocyanates with polyalkylene oxide amines and aminobenzonitriles using the above-described two-step reaction, or by reacting polyalkylene oxide isocyanates and benzonitrile isocyanates with an alkyl diamine, again using a two-step reaction.

The stoichiometry and reaction conditions for attaching the benzonitriles to the polyalkylene oxides are well understood and essentially conventional. The reactions are carried out in solvents in which the reactants are soluble, such as methanol. Reaction temperatures between 0° C. and 10° C. are suitable, and temperatures between 5° C. and 8° C. are preferred. Again, all materials must be essentially water-free.

The adaption of the above reactions to obtain a bifunctional polyalkylene oxide is also well understood by one of ordinary skill in the art. (See, Buckmann et al., *Makromol. Chem.*) Meta- and para-substituted benzonitriles are suitable for use with the present invention, although para-substituted benzonitriles are preferred because they are commercially available.

The aryl imidate activated polyalkylene oxides are purified from low molecular weight materials by conventional methods. The polyalkylene oxide aryl imidate can then be reacted with biologically active nucleophiles to form a linkage between the polyalkylene oxide and the biologically active nucleophile. The resulting product represents a biologically active conjugate of the nucleophile and the polyalkylene oxide.

The term "hydrolytically stable" means that the aryl imidates of the present invention, in aqueous solution, will not undergo substantial degradation at physiological pH up to 27° C. Degradation of less than 50% under these conditions over an eight hour time period is considered insubstantial. At 4° C., substantially less degradation is expected.

The term "biologically active" is used with respect to the nucleophiles of the present invention consistently with the meaning commonly understood to those of ordinary skill in the art, which meaning is not limited to physiological or pharmacological activities of the nucleophiles in the therapeutic sense. For example, many physiologically active nucleotides such as enzymes, the polyalkylene oxide conjugates of which may not have therapeutic applications, are able to catalyze reactions in organic solvents. Likewise, regardless of the therapeutic uses for polyalkylene oxide conjugates of proteins such as concanavalin A, immunoglobulins, and the like, the polyalkylene oxide conjugates of these proteins are also useful as laboratory diagnostic tools.

The polyalkylene oxide conjugates of the biologically active nucleophiles of the present invention are biologically active and possess numerous therapeutic applications. Mammals in need thereof may be treated by administering a therapeutically effective amount of the biologically active polyalkylene oxide conjugates of the biologically active nucleophiles of the present invention.

Therefore, the biologically active nucleophiles of interest to the present invention include a variety of enzymes, including, but not limited to, carbohydrate-specific enzymes, proteolytic enzymes, and the like. Enzymes of interest, for both biological applications in general and therapeutic applications in particular include the oxidoreductases, transferases, hydrolases, lyases, isomerases and ligases disclosed by U.S. Pat. No. 4,179,337, the disclosure of which is hereby incorporated herein by reference thereto. Without being limited to particular enzymes, examples of specific enzymes of interest include asparaginase, arginase, adenosine deaminase, superoxide dismutase, catalase, chymotrypsin, lipase, uricase and bilirubin oxidase. Carbohydrate-specific enzymes of interest include glucose oxidase, glucosidase, galactosidase, glucocerebrosidase, glucuronidase, etc.

The biologically active nucleophiles of the present invention also include proteins of general biological or therapeutic interest, including, but not limited to, hemoglobin and serum proteins such as Factor VIII, Factor IX, immunoglobulins, lectins, interleukins, interferons and colony stimulating factors, and ovalbumin and bovine serum albumin (BSA). Other proteins of general biological or therapeutic interest include hormones such as insulin, ACTH, glucagon, somatostatin, somatotropins, thymosin, parathyroid hormone, pigmentary hormones, somatomedins, erythropoietin, luteinizing hormone, hypothamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Certain of the above proteins such as the interleukins, interferons and colony stimulating factors also exist in non-glycosilated form, usually the result of preparation by recombinant protein techniques. The non-glycosilated versions are also among the biologically active nucleophiles of the present invention.

Other proteins of interest are allergen proteins disclosed by Dreborg et al., Crit. Rev. Therap. Drug Carrier Syst., 6, 315–65 (1990) as having reduced allergenicity when conjugated with polyalkylene oxides, and consequently suitable for use as tolerance inducers. Among the allergins disclosed are Ragweed Antigen E, honeybee venom, mite allergen, and the like.

Other biologically active nucleophiles of the present invention include oligonucleotides, the coupling of which to polyalkylene oxides is disclosed by the above-cited U.S. Pat. No. 4,904,582, and therapeutically active nucleophilic compounds, such as the dihydropyridine calcium channel blockers, the coupling of which with polyalkylene oxides is disclosed by the above-cited U.S. Pat. No. 5,160,734.

One or more polyalkylene oxides can be attached covalently to the biologically active nucleophile by reacting the aryl imidate activated polyalkylene oxide with the nucleophile. The aryl imidate reacts with the nucleophile to form a linkage covalently bonding the nucleophile to the polyalkylene oxide. When the nucleophile is a protein or polypeptide, conjugation occurs at the $\epsilon$-$NH_2$ moieties of lysines to form linkages containing stable amidate moieties.

For nucleophiles such as polypeptides, more than one polyalkylene oxide conjugate per nucleophile is preferred. The degree of conjugation is limited only by the number of available $\epsilon$-$NH_2$ moieties of lysines. The optimum degree of conjugation can be readily determined for a particular nucleophile by one of ordinary skill in the art without undue experimentation. The degree of conjugation may be modified by varying the reaction stoichiometry by well-known techniques.

The reaction of aryl imidate activated polyalkylene oxides with the epsilon-$NH_2$ moieties of polypeptide lysines to form an amidate linkage is illustrated by the reaction sequence depicted below in which R, L, X and $R_1$ are the same as described above with respect to Formula I and $R_4$ represents the balance of the polypeptide:

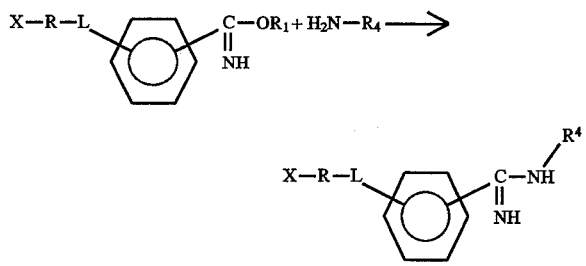

The biologically active nucleophiles may be reacted directly with the aryl imidate activated polyalkylene oxides in an aqueous reaction medium. This reaction medium may also be buffered, depending upon the pH requirements of the nucleophile. The optimum pH for the reaction is generally between about 6.5 and about 8.0 and preferably about 7.4.

In all instances, the optimum reaction medium pH for the stability of particular nucleophiles and for reaction efficiency, and the buffer in which this can be achieved, is readily determined within the above ranges by those of ordinary skill in the art without undue experimentation. For purposes of this application, the operativeness of the within reactions under mild conditions is defined as meaning that the preferred temperature range is between about 4° and about 37° C.

Those of ordinary skill in the art will understand that the reactions will run somewhat faster to completion at higher temperatures, with the proviso that the temperature of the reaction medium cannot exceed the temperature at which the nucleophile may denature or decompose. Furthermore, those of ordinary skill in the art will understand that certain nucleophiles, particularly polypeptides, will require reaction with the aryl imidate activated polyalkylene oxides at reduced temperatures to minimize loss of activity and/or to prevent denaturing. The reduced temperature required by particular polypeptides is preferably no lower than 4° C. and in no event should this temperature be lower than 0° C. The reaction will still take place, although longer reaction times may be necessary.

Usually, the nucleophile is reacted in aqueous solution with a quantity of the aryl imidate activated polyalkylene oxide in excess of the desired degree of conjugation. Following the reaction, the conjugated product is recovered and purified by diafiltration, column chromatography or the like.

In view of the foregoing, it can be readily appreciated that the aryl imidate activated polyalkylene oxides of the present invention possess the optimum balance of reactivity and hydrolytic stability so that polymer conjugates can be formed with biologically active nucleophiles with an insubstantial amount of hydrolytic degradation of the activated polyalkylene oxide. Thus, reaction yields are increased and process costs are reduced.

The following non-limiting examples set forth hereinbelow illustrate certain aspects of the invention. All parts and percentages are by weight unless otherwise noted, and all temperatures are in degrees Celsius.

EXPERIMENTAL

EXAMPLE 1

Synthesis of m-PEG Aryl Imidate

An aryl imidate activated PEG of Formula I, in which L is —NH—CO—, is prepared by first adding to a clean, dry 250 mL three-neck flask 1.0 g (1.99×10⁻⁴ mole) of m-PEG amine and 200 mL of toluene. The solution is heated, with stirring, to 110° C. to remove water along with 100 mL of toluene. The solution is cooled to 25° C. and 0.056 mL (0.040 g, 3.99×10⁻⁴ mole) of triethylamine is added, followed by 0.33 g (1.99×10⁻³ mole) of 4-cyanobenzoyl chloride.

The mixture is heated at 75°–80° C. for four hours, cooled to 40° C. and filtered through a glass filter while warmed to remove triethylamine hydrochloride. As much toluene as possible is stripped off via rotary evaporation, after which 200 mL of isopropanol is added to the residue, followed by heating to 50° C. with stirring to dissolve. This solution is then cooled to room temperature with stirring to effect precipitation. The precipitate is collected by filtration, washed with 100 mL of isopropanol and dried in a vacuum oven at 4° C.

100 mL anhydrous methanol is added to a clean, dry 300 mL three-neck round bottomed flask and cooled to −10° C. by means of a dry ice bath. HCl gas is added subsurface to the methanol with stirring until it is saturated. 1.0 g of the product from the previous step is dissolved in 2 mL of methylene chloride, which solution is then added to the methanolic HCl with stirring. The reaction mixture is allowed to warm to room temperature and held for eight hours. 150 mL of cold ethyl ether is added to the flask to induce precipitation of the m-PEG aryl imidate. The product is collected by filtering the cold mixture and washing with 10 mL of ethyl ether. The product is then dried in a dessicator at room temperature.

EXAMPLE 2

Conjugation of Bovine Hemoglobin With m-PEG Aryl Impdate

The aryl imidate activated m-PEG of Example 1 is conjugated with bovine hemoglobin by first preparing a 10 mL solution of pH 7.8 phosphate buffer by dissolving 0.1380 g $NaH_2PO_4 \cdot H_2O$, 0.2681 g $Na_2HPO_4 \cdot 7H_2O$ and 0.2338 g NaCl in 7.0 mL deionized water. The pH of the solution is then adjusted to 7.8 with 1.0N NaOH and diluted to 10 mL with deionized water. A 4.0 mL sample of isolated bovine hemoglobin (10.9%, 7.02×10⁻⁶ mole) is measured into a 50 mL jacketed beaker chilled to 8° C. by means of a refrigerated recirculating bath. A thermometer and pH electrode are placed in the hemoglobin, which is stirred magnetically. The pH of the hemoglobin is adjusted to 7.8 with 1.0N NaOH where 1.0N HCl as necessary.

To this is added 0.6515 g of the m-PEG aryl imidate of Example 1 (1.26×10⁻⁴ mole) followed by 4.0 mL of the pH 7.8 phosphate buffer prepared above. The mixture is stirred at 8° C. for one hour while maintaining pH 7.8 with dropwise additions of 1.0N NaOH or 1.0N HCl. After one hour of reaction time, 0.0420 g (2.39×10⁻⁴ mole) of cysteine HCl is added, followed by 0.0095 g (1.26×10⁻⁴ mole) of glycine. The pH is adjusted up to 7.8 using 1.0N NaOH, and the mixture is allowed to stir for 15 minutes. The resulting conjugate of m-PEG and hemoglobin is then stored in a 4° C. refrigerator.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A polyalkylene oxide conjugate comprising:
   a nucleophile having biological activity; and
   at least one water-soluble polyalkylene oxide covalently bonded thereto by a hydrolyrically stable linkage formed by reacting said nucleophile with an aryl imidate activated polyalkylene oxide, having a structure represented by (I):

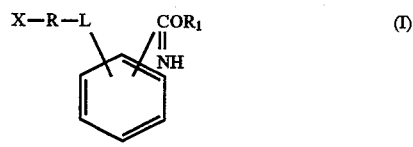

wherein
   R is a water-soluble polyalkylene oxide;
   L is NHC(O) such that the carbonyl is attached to the phenyl ring;
   $R_1$ is a moiety selected from the group consisting of alkyl, phenyl, phenyl alkyl, and cycloalkyl moieties; and
   X is a terminal moiety of said polyalkylene oxide selected from the group consisting of $OH, C_{1-4}$ alkoxy moieties and aryl imidates corresponding to the structure:

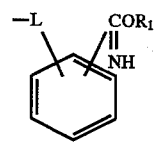

wherein L and $R_1$ are defined as above.

2. The polyalkylene oxide conjugate of claim 1, wherein said polyalkylene oxide is selected from the group consisting of polyethylene glycol and block copolymers of polyethylene glycol and polypropylene glycol.

3. The polyalkylene oxide conjugate of claim 2, wherein said polyalkylene oxide comprises polyethylene glycol.

4. The polyalkylene oxide conjugate of claim 1, wherein said polyalkylene oxide has a number average molecular weight between about 600 and about 100,000 daltons.

5. The polyalkylene oxide conjugate of claim 4, wherein said polyalkylene oxide has a number average molecular weight between about 2,000 and about 20,000 daltons.

6. The polyalkylene oxide conjugate of claim 5, wherein said polyalkylene oxide has a 5,000 dalton number average molecular weight.

7. The polyalkylene oxide conjugate of claim 1, wherein said nucleophile is an enzyme selected from the group consisting of asparaginase, arginase, adenosine deaminase, superoxide dismutase, catalase, chymotrypsin, lipase, uricase, bilirubin oxidase, glucose oxidase, glucosidase, galactosidase, glucocerebrosidase and glucuronidase.

8. The polyalkylene oxide conjugate of claim 1, wherein said nucleophile is a serum protein selected from the group consisting of Factor VIII, Factor IX, interleukins, interferons, colony stimulating factors, immunoglobulins and lectins.

9. The polyalkylene oxide conjugate of claim 8, wherein said nucleophile is an immunoglobulin selected from the group consisting of IgG, IgE, IgM, IgA, IgD and fragments thereof.

10. The polyalkylene oxide conjugate of claim 1, wherein said nucleophile is a hormone selected from the group consisting of insulin, ACTH, glucagon, somatostatin, somatotropins, thymosin, parathyroid hormone, pigmentary hormones, somatomedins, erythropoietin, luteinizining hormone, hypothalmic releasing factors, antidiuretic hormones, prolactin, chorionic gonadotropin, follicle stimulating hormone, tissue plasminogen activator and thyroid-stimulating hormone.

11. The polyalkylene oxide conjugate of claim 1, wherein said nucleophile is a protein selected from the group consisting of hemoglobin, ovalbumin and bovines serum albumin.

12. The polyalkylene oxide conjugate of claim 1, wherein said nucleophile is a polypeptide comprising lysine residues, and at least one of said polyalkylene oxides is covalently bonded to the epsilon-$NH_2$ moiety of said lysine residue via a linkage forming an amidate moiety with said epsilon-$NH_2$ moiety.

13. The polyalkylene oxide conjugate of claim 1, comprising a plurality of polyalkylene oxides covalently bonded to said nucleophile.

14. The polyalkylene oxide conjugate of claim 1, wherein $R_1$ is a moiety selected from the group consisting of methyl, ethyl, phenyl, benzyl and cyclohexyl moieties.

15. The polyalkylene oxide conjugate of claim 1, wherein X is a methoxy moiety.

16. A method of forming a biologically active conjugate of a biologically active nucleophile and one or more water-soluble polyalkylene oxides covalently bonded thereto, said method comprising the steps of:

providing a biologically active nucleophile;

contacting said nucleophile with one or more aryl imidate activated polyalkylene oxides, so that a biologically active conjugate of said biologically active nucleophile and said polyalkylene oxides is formed; and recovering said biologically active conjugate.

17. The method of claim 16, wherein said contacting is carried out in an aqueous reaction medium.

18. The method of claim 17, wherein the pH of said aqueous reaction medium is between about 6.5 and about 8.0.

19. The method of claim 18, wherein the pH of said reaction medium is about 7.4.

20. The method of claim 16, wherein said contacting is carried out at a temperature of from about 4 to about 37 degrees C.

* * * * *